United States Patent [19]

Newkome et al.

[11] Patent Number: 5,154,853
[45] Date of Patent: Oct. 13, 1992

[54] UNIMOLECULAR MICELLES AND METHOD OF MAKING THE SAME

[75] Inventors: George R. Newkome; Charles Moorefield, both of Temple Terrace, Fla.

[73] Assignee: University of South Florida, Tampa, Fla.

[21] Appl. No.: 657,683

[22] Filed: Feb. 19, 1991

[51] Int. Cl.$^5$ .................. B01J 13/00; B01F 17/30
[52] U.S. Cl. ...................... 252/311; 252/351; 252/356; 252/DIG. 2; 252/DIG. 15; 521/50; 528/397; 528/422; 528/425
[58] Field of Search ............... 252/351, 356, DIG. 2, 252/DIG. 15, 311; 528/422, 425, 397; 521/50

[56] References Cited

U.S. PATENT DOCUMENTS 3,813,345   5/1974   Urton .................................. 252/312
4,615,819  10/1986   Leng et al. .......................... 252/110
4,692,275   9/1987   Secemski et al. ................... 252/534
4,801,400   1/1989   Login et al. ......................... 252/357
5,037,910   8/1991   Cook et al. .......................... 526/128
5,039,451   8/1991   Phillips et al. ..................... 252/356

Primary Examiner—Richard D. Lovering
Assistant Examiner—N. Bhat
Attorney, Agent, or Firm—Reising, Ethington, Barnard, Perry & Milton

[57] ABSTRACT

In accordance with the present invention there is provided a method of making a cascade polymer including the steps of alkylating the branches of a multi-branch core alkyne building block including multiple ether side chains and simultaneously reducing the alkyne triple bonds and deprotecting to form a multi-hydroxyl terminated, multi-branched all alkyl polymer. The inventive method results in the formation of a unimolecular micelle consisting essentially of alkyl carbon.

30 Claims, 9 Drawing Sheets

XI  C[(CH$_2$)$_8$C[(CH$_2$)$_3$C≡C(CH$_2$)$_3$C[(CH$_2$)$_3$OCH$_2$Ph]$_3$]$_3$]$_4$

XII R = CH$_2$OH
XIII R = CO$_2$H

1. CH$_2$Cl$_2$, SOBr$_2$, Pyr
2. 12 eq alkyne 1

H$_2$ (55 psi), 25°C, 24 h
EtOH/THF, 10% Pd-C

C{[(CH$_2$)$_3$C≡C(CH$_2$)$_3$C[(CH$_2$)$_3$OCH$_2$Ph]$_3$}$_4$  IX

C{(CH$_2$)$_8$C[(CH$_2$)$_3$OH]$_3$}$_4$   X

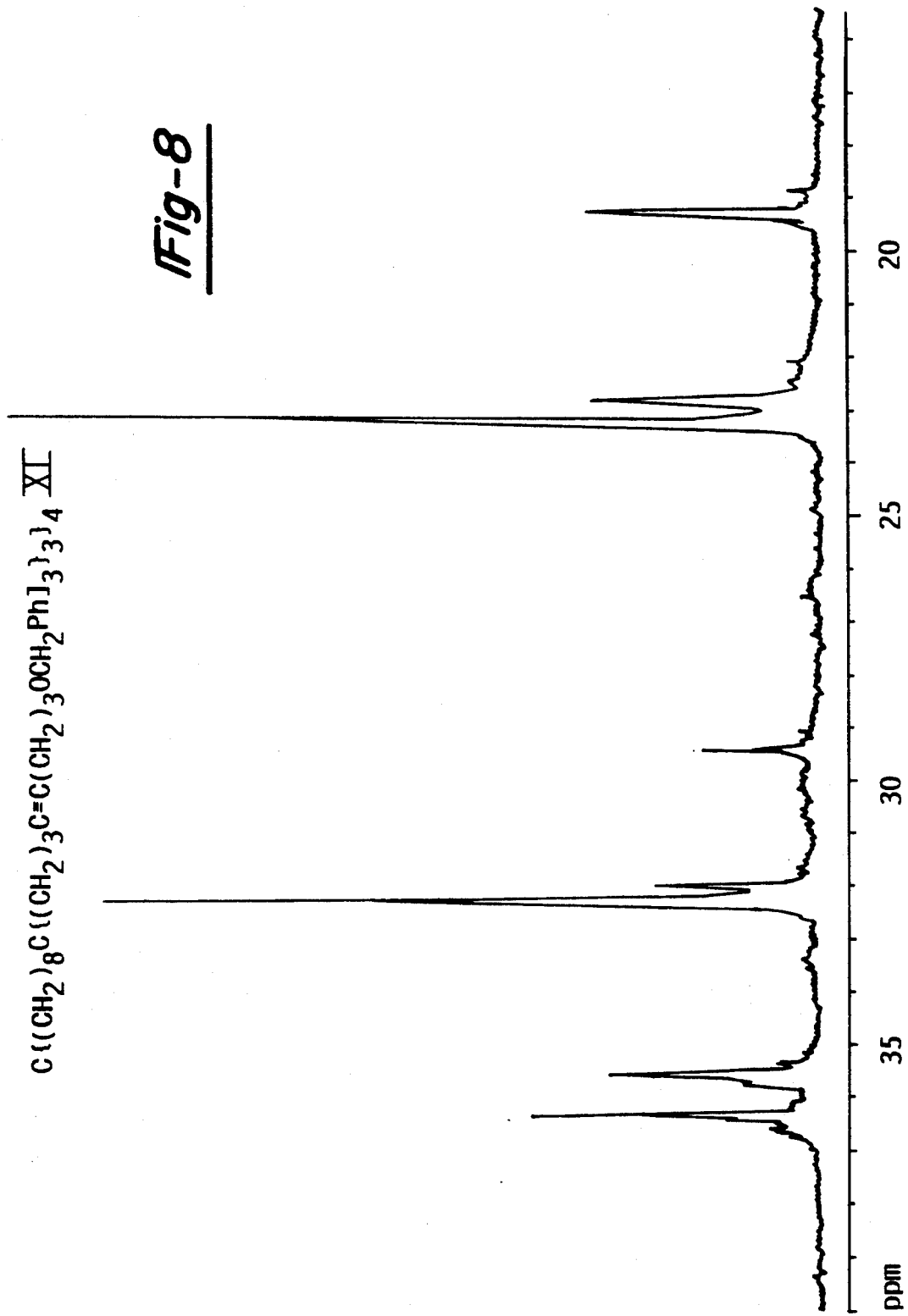

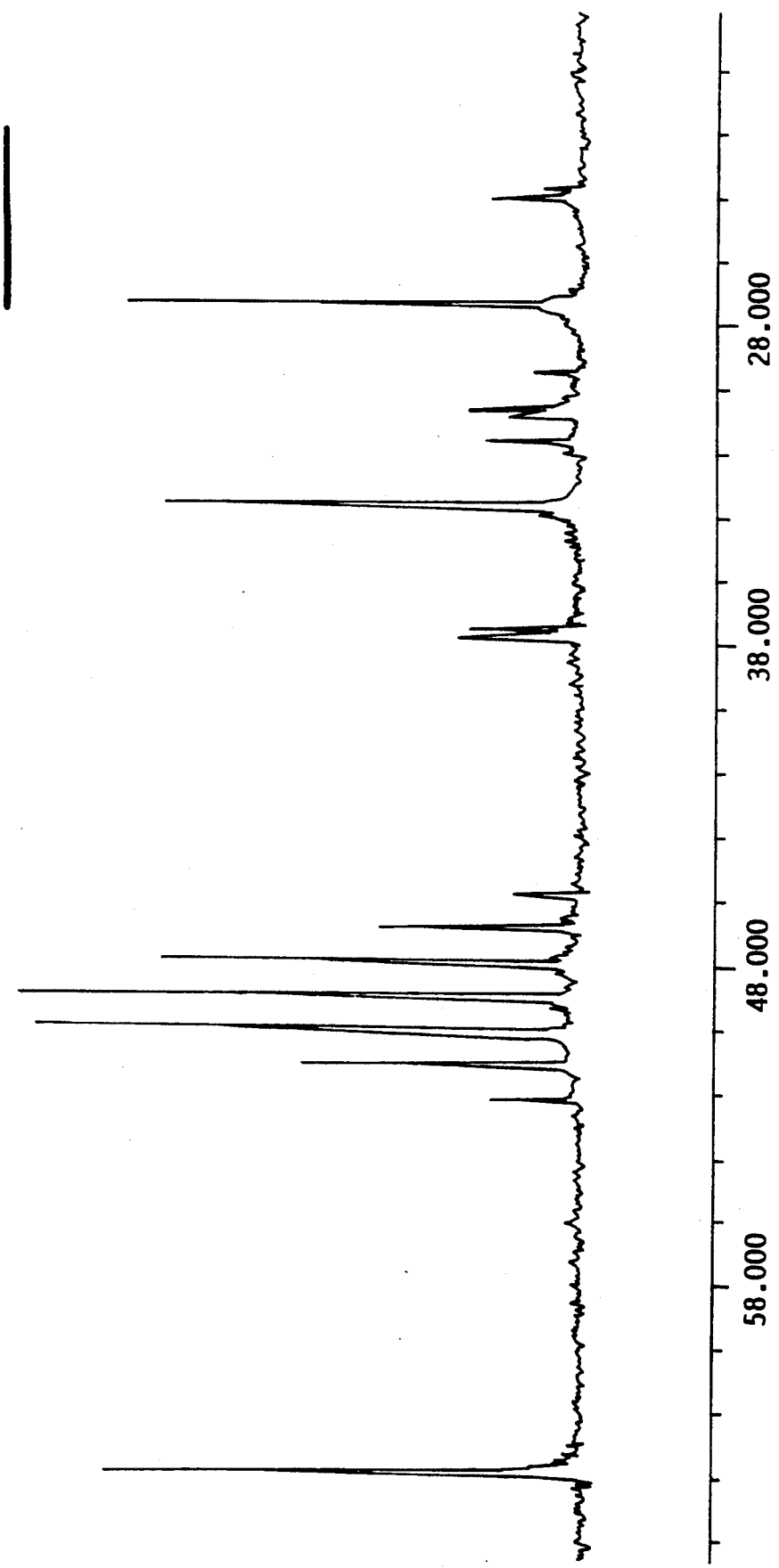

UNIMOLECULAR MICELLES AND METHOD OF MAKING THE SAME

TECHNICAL FIELD

The present invention relates to highly branched molecules possessing a predetermined three dimensional morphology. More specifically, the present invention relates to micelles having uses in areas such as detergents, radioimaging, binding sites for drug delivery, polyfunctional bases and other areas of use.

BACKGROUND ART

The synthesis of high molecular weight, highly branched, multifunctional molecules possessing a predetermined three dimensional morphology has been the focus of a growing number of research groups throughout the world. (1) Synthetic strategies employed for the realization of such cascade polymers require consideration of diverse factors including the content of the initial core, building blocks (or repeat units), spacer molecules, branching numbers, dense packing limits, and desired porosity as well as other factors. The selection of an appropriate building block(s) is governed by the type branching desired, such as carbon versus heteroatom branching, as well as the technology used to attach each successive layer or tier of the cascade polymer. At this time, building block synthons have relied predominantly on heteroatom chemistry for either a center of branching or for attachment of individual building blocks.

Applicants have participated in the design and application of cascade polymers (2). Through applicants, research, high molecular weight molecules were synthesized containing quaternary carbon branching points and a maximum number of terminal functional groups with a focus on the formation of the amide bond. Applicants developed a multiplicative approach utilizing two building blocks, a trialkyl methanetricarboxylate (3) and tris(hydroxymethyl)aminomethane (Tris). From this basic work, applicants have derived a novel method for making the first example of an all alkyl carbon unimolecular micelle.

SUMMARY OF THE INVENTION

In accordance with the present invention there is provided a method of making a cascade polymer including the steps of alkylating the branches of a multi-branch core alkyl compound with a terminal alkyne building block including multiple ethereal side chains and simultaneously reducing the alkyne triple bonds and deprotecting to form a multihydroxyl terminated, multi-branched all alkyl polymer.

The present invention further provides a unimolecular micelle consisting essentially of alkyl carbon possessing terminal functionality.

BRIEF DESCRIPTION OF THE DRAWINGS

Other advantages of the present invention will be readily appreciated as the same becomes better understood by reference to the following detailed description when considered in connection with the accompanying drawings wherein:

FIG. 8 is an expanded $^{13}C$ NMR spectrum of $C\{(CH_2)_8C\{(CH_2)_3C\equiv C(CH_2)_3C[(CH_2)_3OCH_2Ph]_3\}_3\}_4$ (XI); and FIG. 9 is a $^{13}C$ NMR spectrum of $C\{(CH_2)_8C\{(CH_2)_3C[(CH_2)_3OH]_3\}_3\}_4$ (XII).

DETAILED DESCRIPTION OF THE INVENTION

The present invention provides a method of making a cascade polymer which generally includes the steps of alkylating the branches of a multi-branched core alkyl compound with a terminal alkyne building block including multiple ether side chains and then simultaneously reducing the alkyne triple bonds and deprotecting to form a multihydroxyl terminated, multi-branched all alkyl polymer. This all alkyl polymer can be further modified by repetition of the alkylating, reducing and deprotecting steps in sequence to increase the size of the all alkyl polymer.

More specifically, the first step of the method in its broadest sense includes the alkylation of a multi-branched core alkyl compound with a terminal alkyne building block. The two compounds are derived through a similar step reaction process. This process is derived from the previous work by inventors discussed above (3).

By way of background, to circumvent the use of extraneous steps to incorporate a spacer moiety (4), due to the inertness of nucleophilic substitution at the terminal neopentyl carbons, bis-homotris was prepared (5). In general, pursuant to applicants, prior discoveries, it has been found the three carbon atoms are necessary to insure an appropriate distance to minimize the reaction retardation caused by an adjacent quaternary center. Therefore, $C[(CH_2)_3Br]_4$ and $Y(CH_2)_2C[(CH_2)_3X]_3$ were selected previously as the ideal alkyl core (6) and building blocks, respectively.

Figure 1:
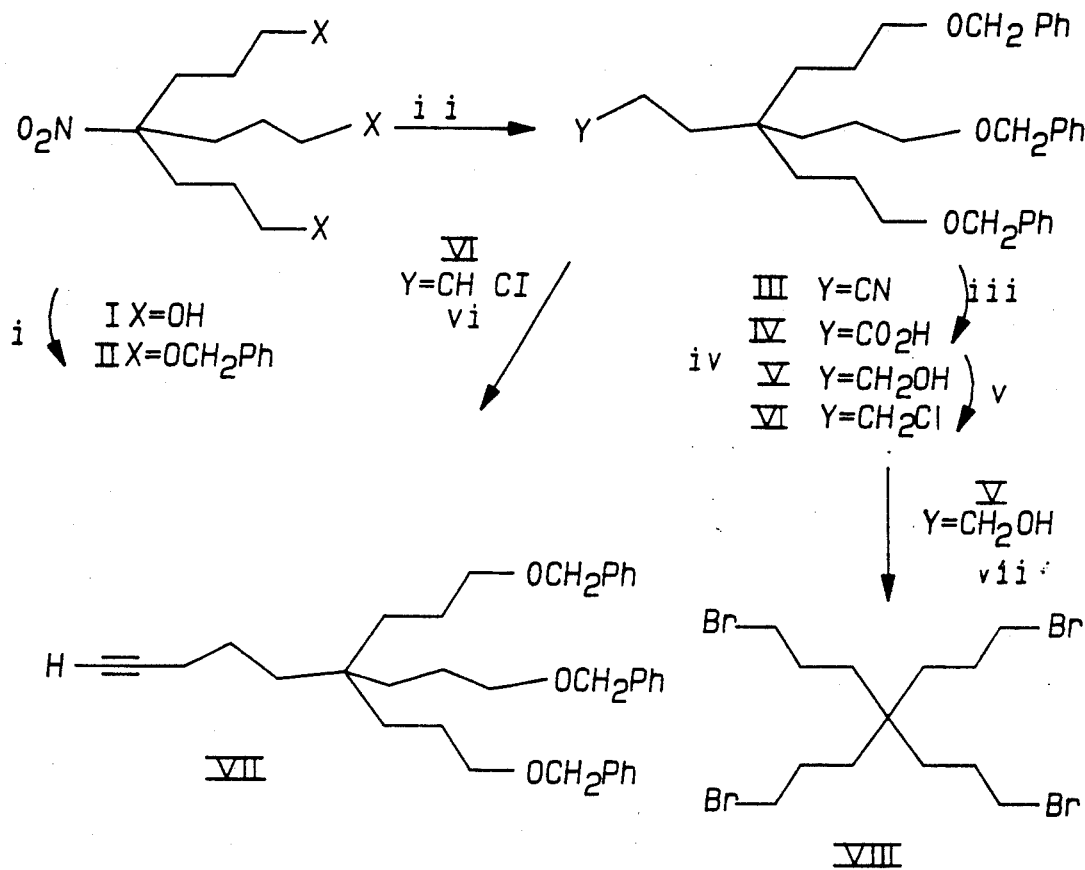
FIG. 1 schematically shows reaction steps for producing intermediates for preparing the micelles in accordance with the present invention.

Taking this prior discovery several steps further, and referring specifically to FIG. 1, nitrotriol (I) was pivotal to the preparation of bis-homotris, and was chosen as the starting point for the repetitive procedure to prepare unimolecular micelles in accordance with the present invention (7). Also, a procedure reported by Ono and coworkers (8) is well suited since it provides the 3-carbon homologating (9) methodology from a quaternary center by addition of tertiary radical to an electron deficient alkene, such as an acrylonitrile or methyl acrylate. Although the yield associated with this reaction has been found to vary (30-90%), applicant has prepared a novel series of tetra(bishomologated) analogs of pentaerythritol via this procedure.

Again referring to FIG. 1, 4-nitro-4-[1-(hydroxypropyl)]-1,7-heptanediol(I) was treated (10) with benzyl chloride to give the tris-ether II with a 78% yield. The tris-ether was subsequently cyanoethylated (9) affording a 61% yield of cyanotri(benzylether) III. The characteristic $^{13}$C NMR chemical shifts for the 4° carbon (36.5 ppm), cyano moiety (120 ppm), and CH$_2$CN (11.6 ppm) and the loss of the peak at 94.0 ppm for the nitro substituted carbon support the assignment of III.

Hydrolysis of the nitrile III was made by standard methods (11) and proceeded cleanly to derive a 92% yield of the carboxylic acid IV. This compound was indicated by the new appearance of a peak at 179.8 ppm (CO$_2$H) using $^{13}$C NMR spectroscopy. Conversion of acid IV to an alcohol V proceeded with a yield of greater than 95% when excess 1.0 M BH$_3$/THF solution was used. This reaction product was confirmed with 13C NMR by the absorption at 63.3 ppm (CH$_2$OH). Transformation of V to a chloride VI was achieved at a 92% yield in CH$_2$Cl$_2$ with excess thionyl chloride and a catalytic amount of pyridine (12). This conclusion with regard to the derived compound was supported ($^{13}$C NMR) by a new peak at 45.6 ppm (CH$_2$Cl). Reaction of lithium acetylide ethylenediamine complex (13) in Me$_2$SO with VI gave an 87% yield of the desired terminal alkyne VII. This terminal alkyne was used as the building block of the present invention and was characterized by $^{13}$C NMR by the appearance of new signals at 84.0 (CH$_2$C≡CH) and 68.1 ppm (CH$_2$C≡CH).

Applicant synthesized the core tetrabromide (VIII) from the alcohol V by bromination with HBr/H$_2$SO$_4$. Accordingly, applicants' method utilizes eight steps from nitromethane providing a 24% (overall) yield versus prior art methods including 17 steps from citric acid yielding a less than 2% overall yield (14) or 12 steps from tetrahydropyran-4-one providing a less than 5% overall yield (6).

In view of the above, applicant synthesized the multi-branch core alkyl compound and the terminal alkyne building block from the same original starting material, the nitrotriol I. This reaction sequence provided an efficient route to the desired results and further provides an economically feasible method utilizing common reactions to synthesize the two necessary components of the present invention.

As stated above, the progressive building of the tiers of the cascade polymer results from sequential alkylation, reduction/deprotection and the repetition of the two-step procedure. The specific steps are set forth as follows.

Figure 2:
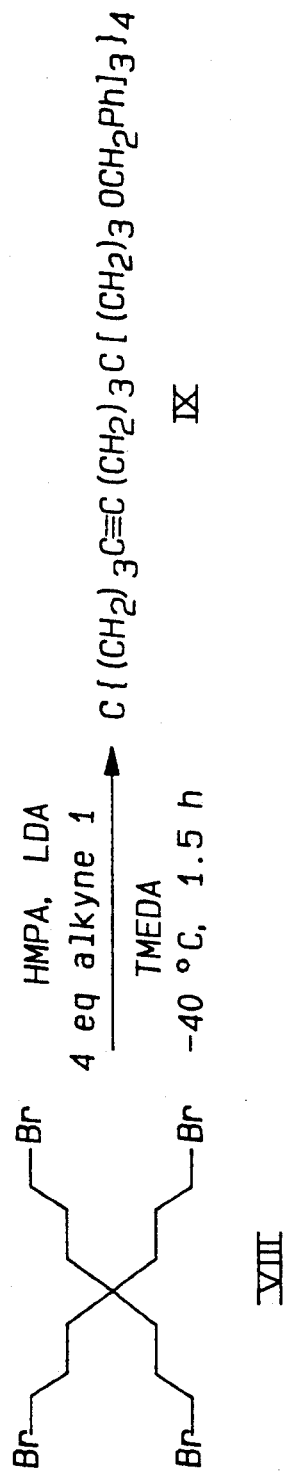
FIG. 2 schematically shows additional reactions in accordance with the subject method.
Figure 2:
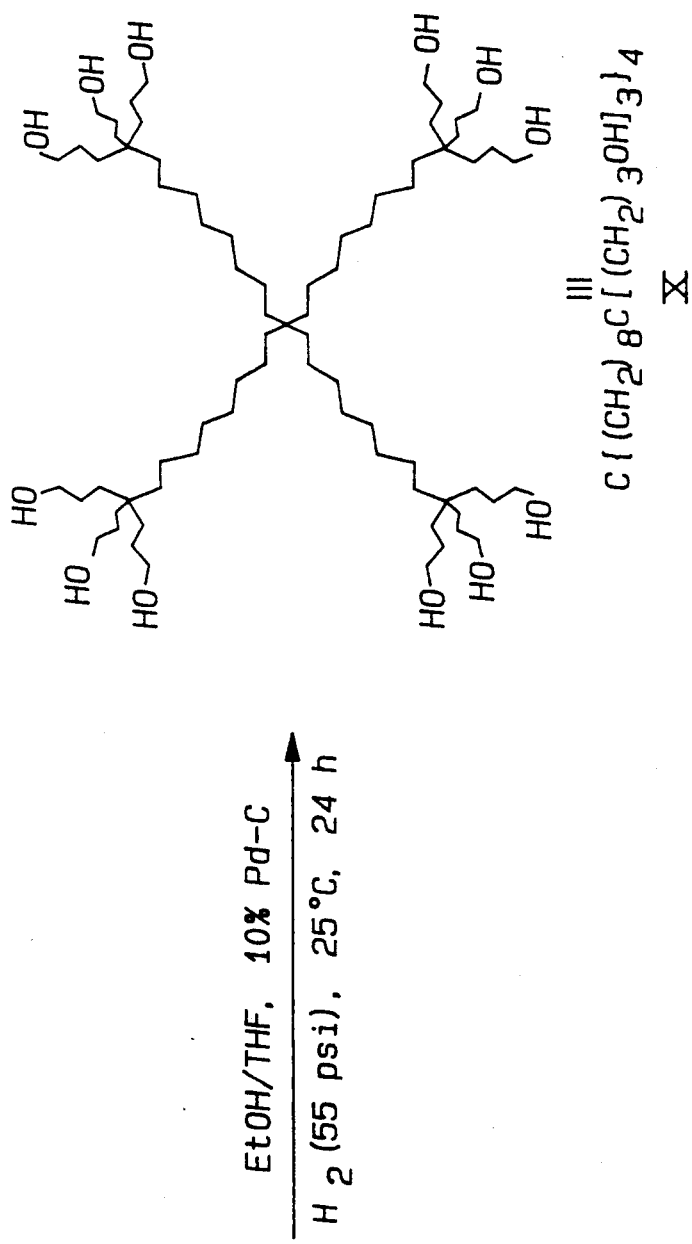
Figure 4:
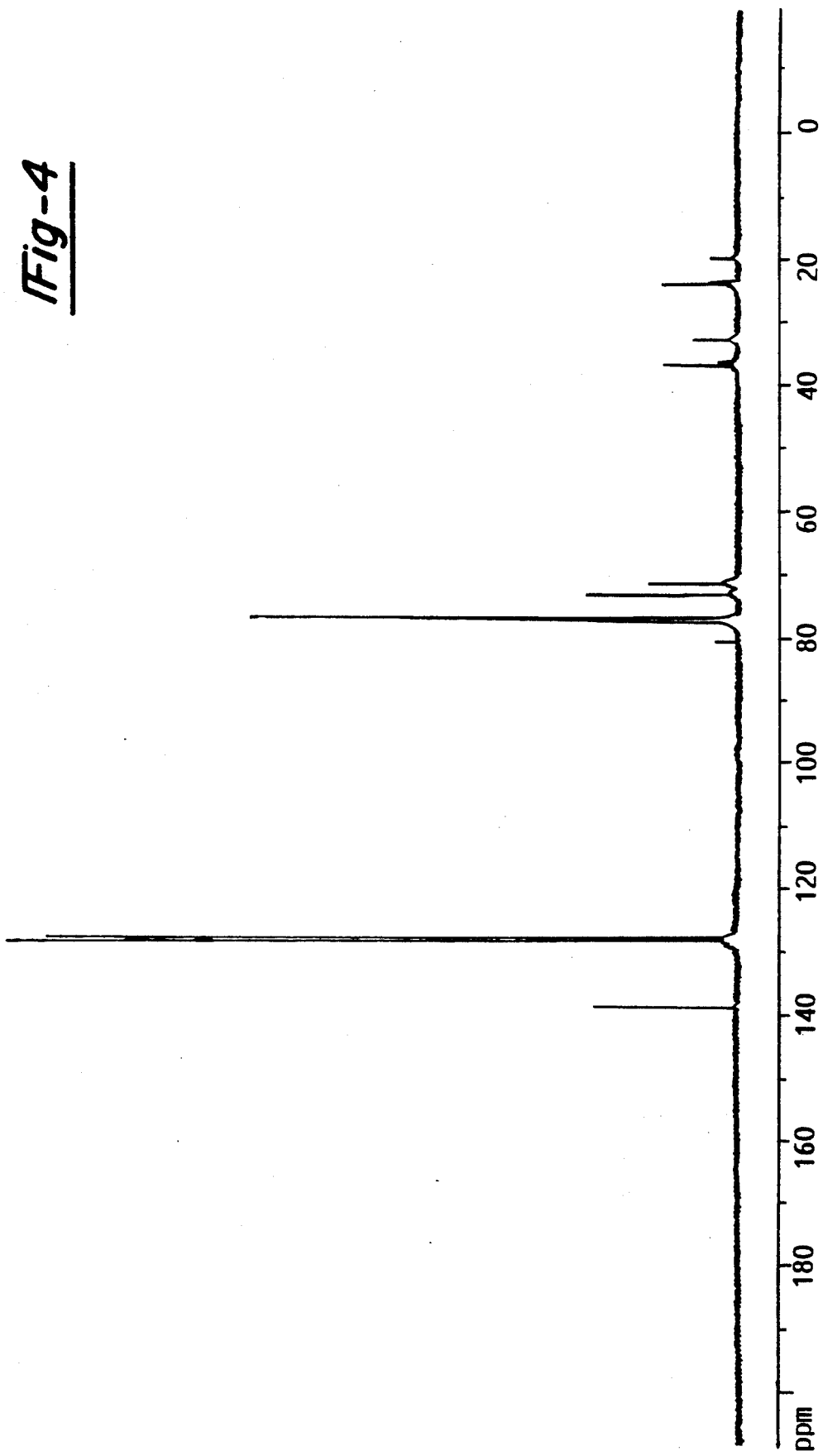
FIG. 4 is a $^{13}C$ NMR spectrum of $C\{(CH_2)_3C\ C(CH_2)_3C[(CH_2)_3OCH_2Ph]_3\}_4$ (IX)
Figure 5:
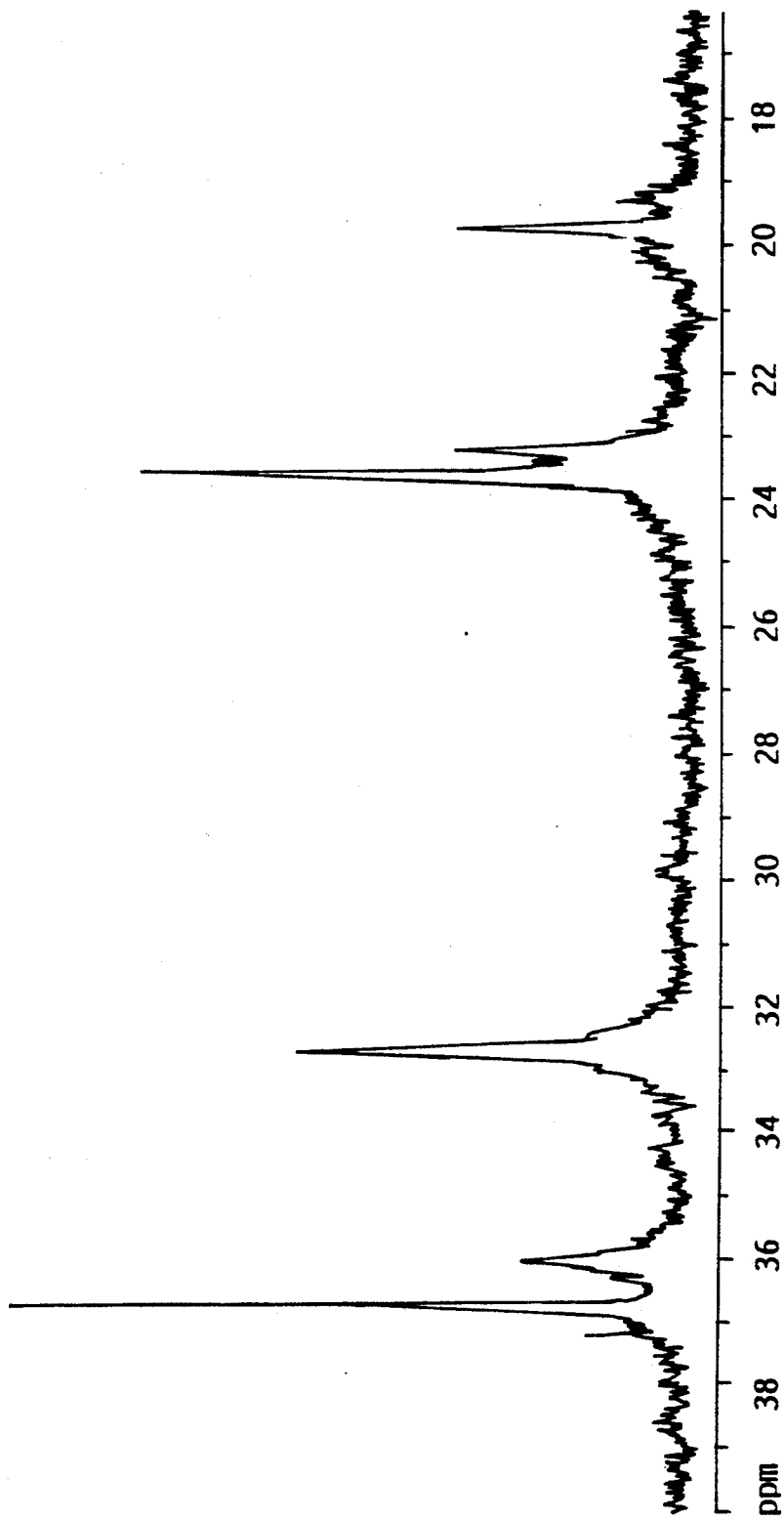
FIG. 5 is an expanded $^{13}C$ NMR spectrum of $C\{(CH_2)_3C\ C(CH_2)_3C[(CH_2)_3OCH_2Ph]_3\}_4$ (IX)

Alkylation of the four-directional core VIII is accomplished with four or more equivalents of the terminal alkyne building block VII, as shown in FIG. 2. The alkylation is accomplished using hexamethylphosphoramide (HMPA), tetramethylethylenediamine (TMEDA) and lithium diisopropylamide (LDA) giving a 67% yield of the purified dodecabenzyl ether (IX) pursuant to methods previously disclosed (15). This conversion was evidenced by the disappearance of the terminal alkyne absorptions and the appearance of a peak at 80.9 ppm (C≡C). The structure of IX via $^{13}$C NMR and $^1$H NMR analysis being shown in FIGS. 4 and 5).

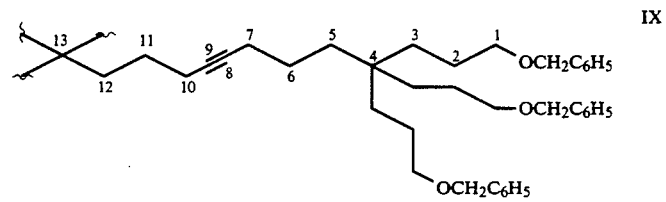

1,25-Dibenzyloxy-8,17-diyne-13,13-bis[12-benzyloxy-9,9-bis(3-benzyloxypropyl)dodecyl-1-yne]-4,4,22,22-tetrakis(3-benzyloxypropyl)pentacosane(IX).

$^{13}$C NMR (CDCl$_3$) δ 19.8 (C-7, C-10), 23.1 (C-6, C-11), 23.3 (C-2), 32.1 (C-3), 36.0 (C-5, C12), 36.8 (C-4), 37.1 (C-13), 71.0 (C-1), 72.6 (OCH$_2$C$_6$C$_5$), 80.1 (C-8, C-8, C-9), 127.3, 128.1, 138.4 (C$_6$H$_5$). $^1$H NMR (CDCl$_3$) δ 1.10–1.65 (m, 80 H), 2.00–2.21 (m, 16 H), 3.35 (br t, 24 H), 4.45 (S, 24 H), 7.28 (s, 60 H).

Figure 6:
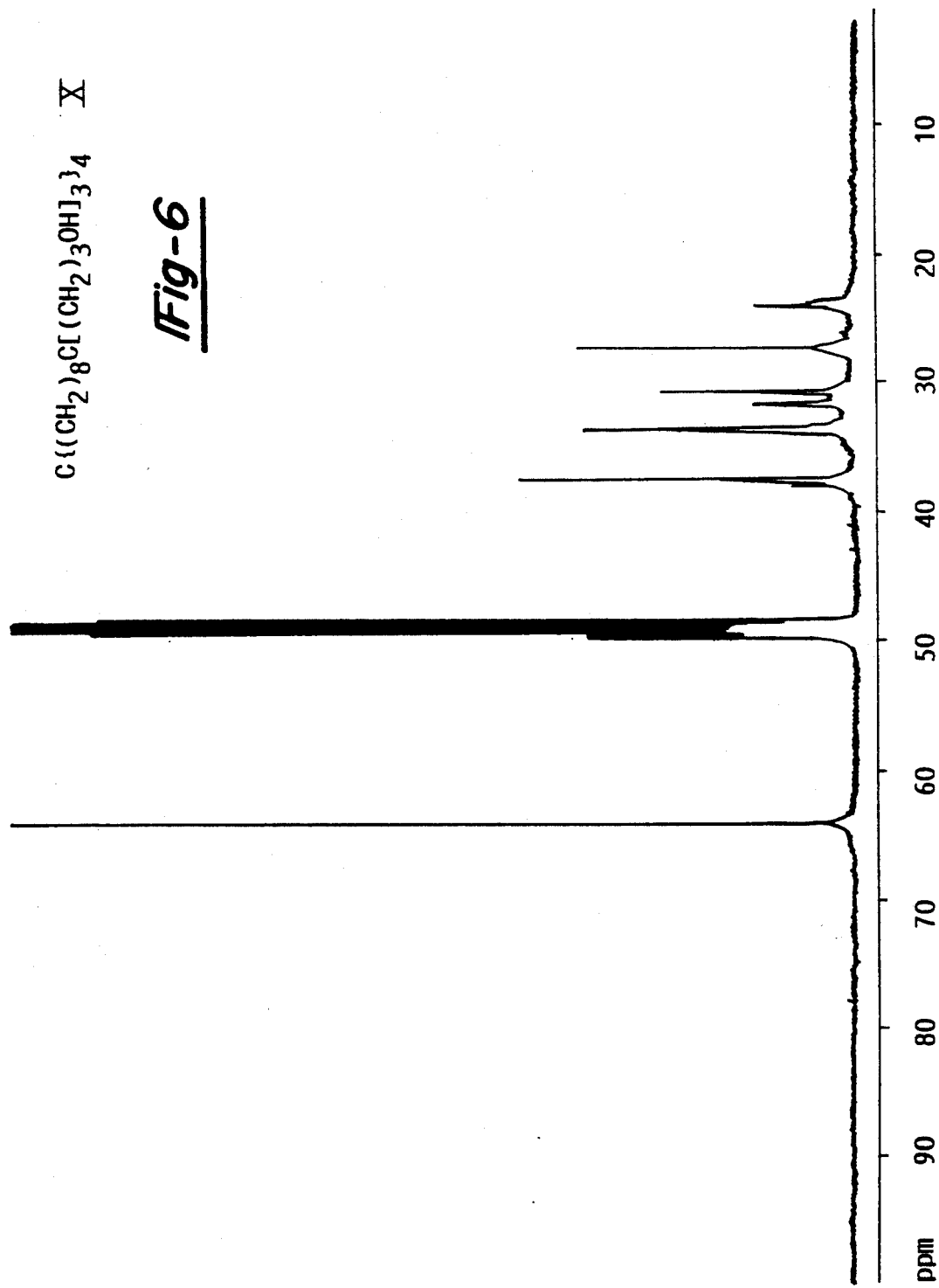
FIG. 6 is a $^{13}C$ NMR spectrum of $C\{(CH_2)_8C[(CH_2)_3OH]_3\}_4$ (X)

The alkylation step is followed by the simultaneous reduction of the triple bonds and the deprotection in accordance with the present invention. The simultaneous reduction and deprotection of IX are accomplished with Pd-C under hydrogen at 3 atmospheres. This procedure afforded a 91% yield of the dodecaalcohol X. As shown by the following data from $^{13}$C NMR and $^1$H NMR and as indicated by the structure set forth below, as well as the graphic spectographic data shown in FIG. 6, the results were indicated by the disappearance of absorptions assigned to alkyne carbons and the carbons alpha to the triple bonds (19.8 ppm as well as the appearance as a peak at 64.1 ppm) (CH$_2$OH).

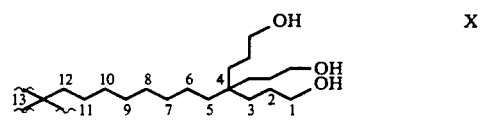

1,25-Dihydroxy-13,13-bis[12-hydroxy-9,9-(3-hydroxypropyl)dodecyl]-4,4,22,22-tetrakis(3-hydroxypropyl)-pentacosane (X).

$^{13}$C NMR (CD$_3$OD) δ 23.9, 24.1 (C-6, C-11), 27.4 (C-2), 30.8 (C-8, C-9, C-13), 31.7, 31.8 (C-10, C-7), 33.6 (C-3), 37.5 (C-4), 37.8, 38.1 (C-5, C-12), 63.8 (C-1). $^1$H NMR (CD$_3$OD) δ 1.08–1.32 (m, 112 H), 3.37 (t, 245 H, J=6.5 Hz).

Figure 3:
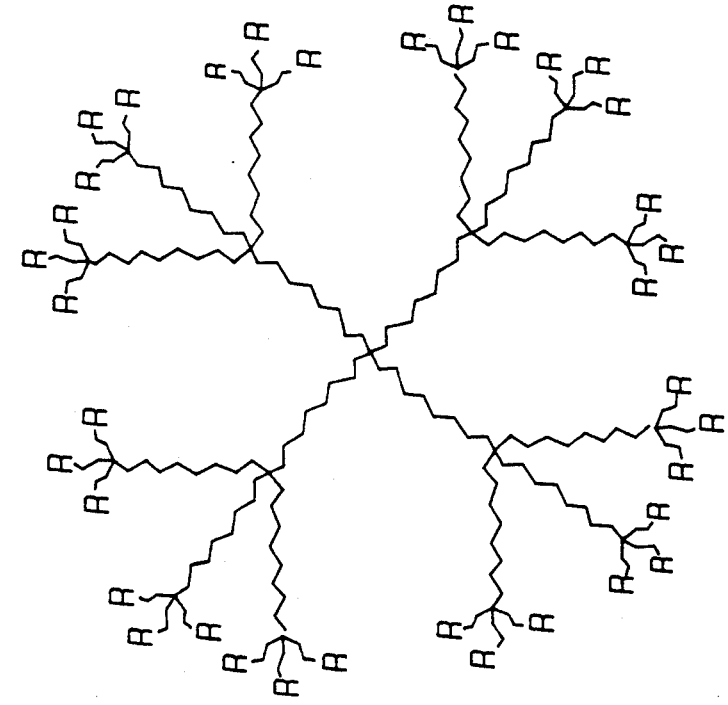
FIG. 3 schematically shows the reactions for creating an additional tier or layer of the micelle in accordance with the present invention.
Figure 7:
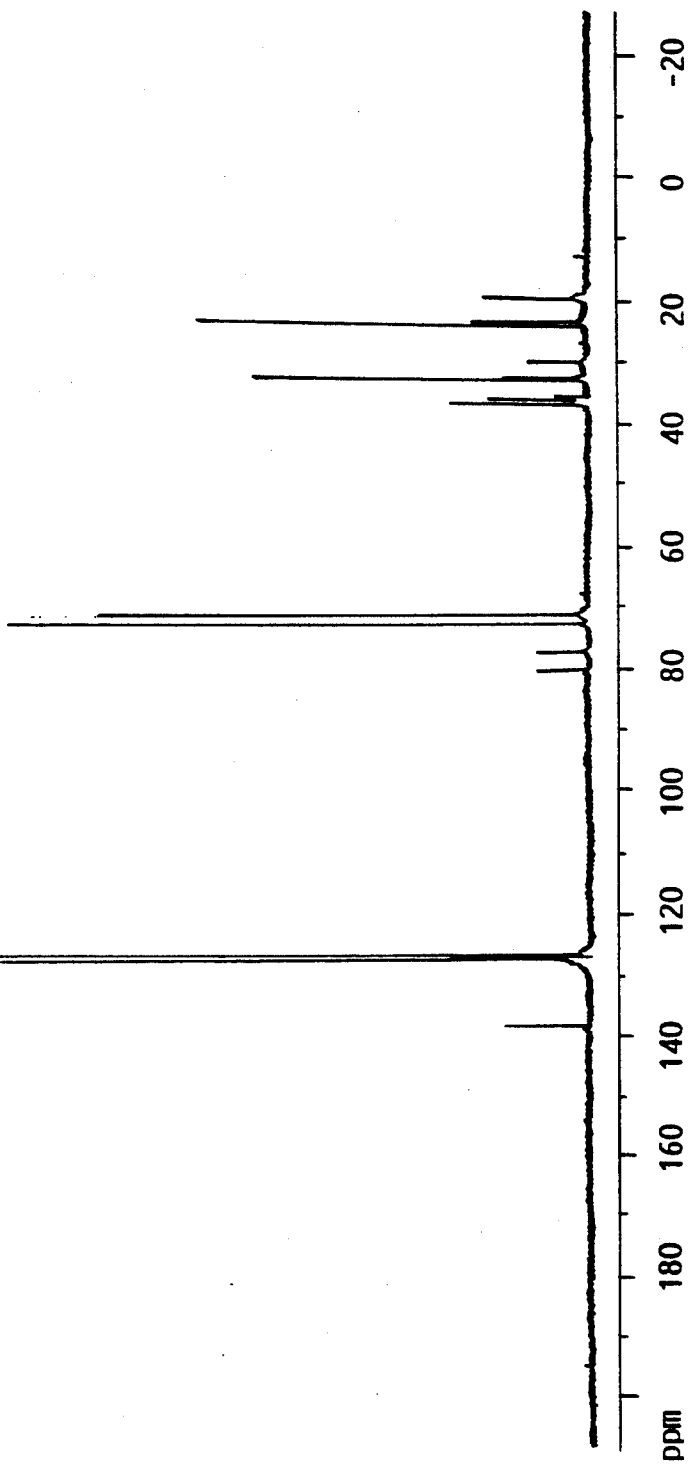
FIG. 7 is a $^{13}C$ NMR spectrum of $C\{(CH_2)_8C\{(CH_2)_3C\ C(CH_2)_3C[(CH_2)_3OCH_2Ph]_3\}_3\}_4$ (XI)

In order to add an additional tier to the polymer, the alcohol X was converted to the dodecabromide employing SOBr$_2$ at 40° C. for 12 hours resulting in a 53% yield (34.8 ppm:CH$_2$Br). As shown in FIG. 3, the second tier was readily obtained by alkylation of the dodecabromide resulting from the bromination of X with 12 or more equivalents of the alkyne building block VII to give a 49% yield of the hexatricontabenzylether XI, the structure of which being shown below as the spectographic data, the graphics of the spectroscopy being shown in FIGS. 7 & 8.

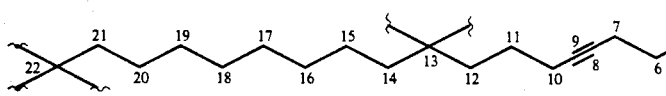
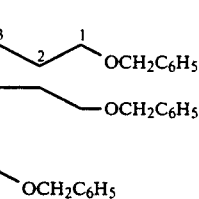

XI $^{13}$C NMR (CDCl$_3$) δ 19.3 (C-7, C-10), 22.8 (C-6, C-11, C-15, C-20), 23.2 (C-2), 29.4 (C-17, C-18, C-22), 31.9 (C-16, C-19), 32.3 (C-3), 35.5 (C-14), C-21, C-12, C-5), 36.3 (C-4, C-13), 71.0 (C-1), 72.6 (OCH$_2$C$_6$H$_5$), 80.1 (C-8, C-9), 127.2, 127.3, 128.0, 138.3 (C$_6$H$_5$ ); $^1$H NMR (CDCl$_3$) δ 1.05–1.70 (m, 300 H), 2.00–2.22 (m, 48 H), 3.36 (br t, 72 H), 4.43 (s, 72 H), 7.27 (s, 180 H).

XI was similarly reduced and deprotected in one step providing an 89% yield of the hexatricontaalcohol XII. The structure as well as the $^{13}$C NMR and $^1$H NMR data are set forth below, the spectroscopy being in shown in FIG. 9.

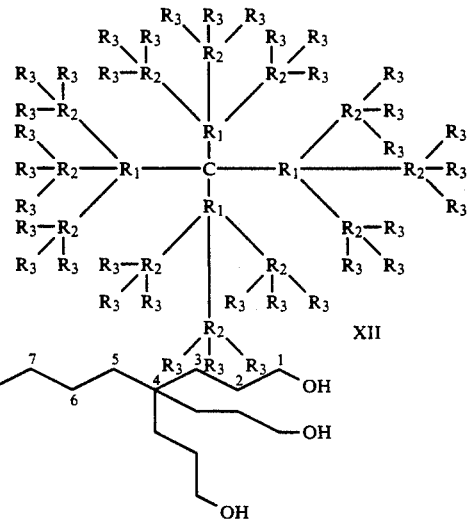

XII

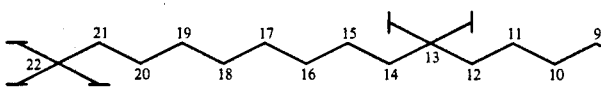

1,43-Dihydroxy-4,4,40,40-tetrakis(3-hydroxyropyl)-13,13,31,31-tetrakis[12-hydroxy 9,9-bis(3-hydroxypropyl)-dodecyl]-22,22-bis[21-hydroxy-18,18-bis(3-hydroxypropyl); 9,9-bis[12-hydroxy-9,9-bis(3-hydroxypropyl)-dodecyl]heneicosyl]tritetrancontane (XII).

$^{12}$C NMR (CD$_3$OD) δ 23.8 (C-15, C-20), 24.0 (C-6, C-11), 27.4 (C-2), 29.5 (C-13, C-22), 30.7, 30.8 (C-8, C-9, C-17, C-18), 31.6 (C-7, (C-10, C-16, C-19), 33.6 (C-3), 37.5 (C-4), 37.7 (C-5, C-12, C-14, C-21), 63.9 (C-1); $^1$H NMR (CD$_3$OD) δ 1.15–1.87 (m, 400 H), 3.50 (t, 72 H, J=6.5 Hz).

Both the polyether XI and the polyalcohol XII exhibited many of the same $^{13}$C NMR signals as their lower analogs, IX, X.

Although the polyol XII is only marginally soluble in water, molecular inclusion of the micellar probe chlortetracycline (CTC) by methods previously reported (16) supports the guest-host relationship and micellar character of XII. CTC is a water soluble dye which is fluorescent only in lipophilic environments.

In accordance with the present invention, the cascade polymer made acts as a micelle. To increase the aqueous solubility of the micelle, XII was oxidized by RuO$_4$ pursuant to previously reported methods (17). The reaction afforded an 85% yield of the hexatricontacarboxylate salt XIII. The disappearance of the absorption for the hydroxymethyl moiety (64.0 ppm) and the appearance of carboxylate signal (187.4 ppm) as well as the high water solubility of the sodium salt support this transformation (the spectographic results not being shown in the Figures). Again the micellar properties of XIII were confirmed by the uniform fluorescence when CTC was added to an aqueous solution of XIII.

The above inventive method sets forth a unique sequence of reactions for deriving for the first time an all alkyl carbon unimolecular micelle having the formula wherein R$_1$ is an alkyl having C$_3$ to C$_{20}$, R$_2$ is an alkyl having C$_3$ to C$_{20}$ and R$_3$ is selected from the group including —CONH$_2$, —COCl, —CHO, —CN, —CO$_2$R$_4$, —COR$_4$, and R$_4$ being ammonium, sulfonium, phosphonium, —H, alkyl, alkaryl, or aryl group(s) or alkaline or alkaline earth metalions. These surface group functionalities can be easily modified by standard chemical processes. Further, other groups such as halogens, bipy, 9,10-phen, amines, sulfur or phosphorus moieties, for example, can be added to/or substituted for the surface group functionalities.

Of course, the unimolecular micelle in accordance with the present invention could have predefined branching, depending upon the number of sequential alkylations, reductions, and deprotections that are performed.

The surface of the unimolecular micelle can be readily coated with metal ions. All mono-, di-, and trivalent metals are possibly bonded directly (with bipy) or indirectly through —CO$_2$ $^-$bonds.

The alkyl carbon surrounded by the branched arms of the micelle define a core therewithin. The incorporation of a single nitrogen, oxygen, sulfur, or phosphorus molecule into the molecular core, per arm or branch of the micelle, permits the inclusion of metals as well as organics into the micelle infrastructure.

It is further possible to incorporate chirality into either the core region or surface thereby creating a chiral sphere with an objectively active surface for resolution of achiral mixtures. This can be accomplished by incorporating chiral moieties e.g. naturally occurring amino acids or resolved molecules of known chirality either at the core or in or on the branching arms. Polyacids upon treatment with protected amino acids in the presence of DCC afforded the protected polyamino acid, which is deprotected and subjected to the above iterative procedures.

The micelle made in accordance with the present invention has a predetermined porosity created by the relationships of the branches, the core defined above, and each of the quaternary centers created by each additional tier layered thereon. The porosity of the inside core can be changed by increasing or decreasing the distances between the quaternary centers, that is by changing the branch arm lengths (R1, R2 ... ).

By changing the surface character of the micelles made in accordance with the present invention, various uses can be developed for the micelles. For example, a $-CO_2^-$ surface can be created thereby rendering the micelles useful for detergents (soaps) and surfactants. Iodine can be incorporated onto the surface of the micelles for use of the micelles in radioimaging. Hydroxyl groups can be incorporated onto the surface of the micelles for use of the micelles as detergents and for binding sights for drug delivery. Amine surface functionalization can be created on the micelles to provide a polyfunctional base (organic). A bipy surface can be created for metal ion sequestering. A bipy metal surface can be created for chemical catalysts. Further, $-CONHR_1$ can be created for chiral recognition and molecular recognition. Of course, the surface of the all aliphatic four directional cascade polymer be modified for many other uses.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

REFERENCES 1. (a) Chemistry of Micelles Series. Part 10. Newkome, G. R. Presented at the Symposium on Self-assembling Structures at the 199th National Meeting of the American Chemical Society, Boxton, MA, April 1990; ORGN 317. Preceding paper, see: Broussard, M.; Juma, B.; Fronczek, F. R.; Watkins, S. F.; Newkome, G. R.; Moorefield, C. N. Acta Cryst. 1990, in press. (b) Visiting scholar, University of the West Indies, Jamaica, 1989–1990. (c) Visiting Scholar, Sampalpur University, 1988–1990.
2. Tomalia, D. A., et. ao.,; *Agnew. Chem. Int. Ed. Engl.* 1990, 29, 138 and refs cited therein. Kim, Y. H.; Webster, O. W. *J. Am. Chem. Soc.,* 190 112, 4592.
3. (a) Newkom, G. R. et. al., *J. Org. Chem.* 1985, 50, 2003. (b) Newkome, G. R. et. al., *J. Am. Chem. Soc.* 1986, 108, 849. (c) Newkome, G. R. et. al., *J. Chem. Soc., Chem. Commun.* 1986, 752. (d) Newkom, G. R. Et. al., *J. Am. Chem. Soc.,* 1990, 112, 8458.
4. Newkome, G. R. et. al., *Org. Prep. & Procedure Inc.* 1986, 18, 451. Skarzewski, J. Tetrahedron 1989, 45, 4593.
5. Newkome, G. R. et. al., *J. Org. Chem.* 1988, 53, 5552.
6. Newkome, G. R. et. al., *J. Org. Chem.* 1987, 52, 5480.
7. Available from Aldrich Chemical Co. Catalog #36,153-4
8. Ono, N. et. al., *Tetrahedron* 1985, 41, 4013.
9. Rice, L. M. et. al., *J. Pharm. Chem.,* 1971, 60, 1760.
10. Iwashige, I. et. al., *Chem. Pharm. Bull.,* 1967, 15, 1803.
11. Vogel, A. I. *Textbook of Practical Organic Chemistry,* 4th ed. Longmans: London 1978; p. 478.
12. Pizey, *Synthetic Reagents;* Wiley: New York, 1974, 1, pp. 321–357.
13. Smith, W. N. et. al., *Synthesis,* 1974, 441.
14. Ingold, C. K. et. al., *J. Chem. Soc. Trans.* 1922, 1645.
15. All new compounds were obtained analytically pure and characterized by $^{13}C$ NMR, $^1H$ NMR, and IR.
16. Caswell, A. H. et. al., *Biochem. Biophys. Res. Commun.* 1971, 43, 625.
17. Imgartinger, H. et. al., *J. Org. Chem.* 1988, 53, 3046.

What is claimed is:

1. A method of making a cascade polymer includes the steps of: alkylating the branches of a multi-branched core alkyl compound with a terminal alkyne building block including multiple ethereal side chains, and simultaneously reducing the alkyne triple bonds and deprotecting to form a multihydroxyl terminated multi-branched all alkyl polymer.

2. A method as set forth in claim 1 wherein said alkylating, reducing, and deprotecting steps are sequentially repeated to increase the size of the all alkyl polymer.

3. A method as set forth in claim 2 further including the step of oxidizing the multihydroxyl terminations to increase the water solubility of the polymer.

4. A method as set forth in claim 3 wherein said oxidizing step is further defined as oxidizing the multihydroxyl termination in the presence of $RuO_4$ $NaIO_4$ and forming a multi-carboxylate branched polymer.

5. A method as set forth in claim 1 wherein said alkylating step is further defined as alkylating in the presence of hexamethylphosphoramide, lithium diisopropylamide and tetramethylethylemidiamine.

6. A method as set forth in claim 1 wherein said deprotecting step is further defined as deprotecting in the presence of Pd-C under hydrogen.

7. A method as set forth in claim 1 wherein the core alkyl compound includes halogenated side chains, said alkylating step being further defined as alkylating the halogenated side chains.

8. A method as set forth in claim 7 wherein said sequential repeating step is further defined as transforming to a better leaving group each of the multihydroxyl branches and then alkylating each of the transformed branches.

9. A method as set forth in claim 8 wherein in said transforming step is further defined as brominating each of the multihydroxyl branches.

10. A method as set forth in claim 1 wherein the core alkyl compound is a tetrabromide alkyl core compound, said alkylating step being further defined as alkylating the core compound with four equivalents for the terminal alkyne building block and forming a dodecabenzyl ether.

11. A method as set forth in claim 10 wherein said reducing and deprotecting steps are further defined as forming a dodecaalcohol.

12. A method as set forth in claim 11 further including the steps of converting the dodecaalcohol to a dodecabromide in the presence of $SOBr_2$ and initiating further elongation of the branches by repeating said alkylating, reducing, and deprotecting steps.

13. A method as set forth in claim 1 further including the steps of deriving the terminal alkyne building block from a nitrotriol.

14. A method as set forth in claim 13 wherein said deriving step is further defined as deriving the terminal alkyne building block from 4-nitro-4-[1-(hydroxypropyl)]-1,7-heptanediol (I).

15. A method as set forth in claim 13 wherein said deriving step is further defined as treating (I) with benzyl chloride to form a tris ether (II), cyanoethylating (II) to form a cyanotris (benzylether) (III), hydrolyzing the nitrile of (III) to derive a carboxylic acid (IV), converting the acid (IV) to an alcohol (V) with excess $BH_3$-THF solution transforming (V) to a chloride (VI) in $CH_2Cl_2$ with excess thionyl chloride and a catalytic amount of pyridine, reacting (VI) with lithium acetylide ethylenediamine complex in $Me_2SO$ to derive a terminal alkyne (VII).

16. A method as set forth in claim 13 further including the step of synthesizing the core alkyl compound from a nitrotriol.

17. A method as set forth in claim 16 wherein said synthesizing step is further defined as synthesizing the core alkyl compound from (I).

18. A method as set forth in claim 16 wherein said synthesizing step is further defined as treating I with benzyl chloride to form II, cyanoethylating II to form III, hydrolyzing the nitrile of III to derive IV, converting IV to V with excess $BH_3$-THF solution, and brominating V with $HBr/H_2SO_4$ to synthesize the core alkyl tetrabromide.

19. A method as set forth in claim 1 further including the step of modifying the CN, $CO_2R$ or —COR, wherein R is selected from the group consisting of H, alkyl, alkaryl, aryl ammonium, sulfonium, phosphonium and metal salt.

20. A method as set forth in claim 1 further including the steps of bonding mono-, di-, and tri-valent metals to said multihydroxyl terminations.

21. A method as set forth in claim 1 wherein the polymer has a predetermined porosity, said method including the step of changing the porosity of the polymer.

22. A method as set forth in claim 21 wherein each of the core alkyl compound and terminal alkyne building blocks define a quaternary center, said changing step is further defined as changing the distances between quaternary centers.

23. A method as set forth in claim 1 further including the step of incorporating chirality either in a core or on the surface creating a chiral sphere.

24. An unimolecular micelle consisting essentially of a carbon core atom and essentially all alkyl arms extending therefrom.

25. A micelle as set forth in claim 24 wherein said micelle consists essentially of multibranched all alkyl arms having hydroxyl terminations.

26. A micelle as set forth in claim 24 wherein said micelle consists essentially of multi-branched all alkyl arms having carboxyl terminations.

27. A micelle as set forth in claim 24 including a mono-, di-, or tri-valent metal bonded thereto.

28. A micelle as set forth in claim 24 wherein each of said branches includes an N, O, S, or P bonded thereto thereby permitting the inclusion of metals or organics into said core.

29. A unimolecular micelle having the formula

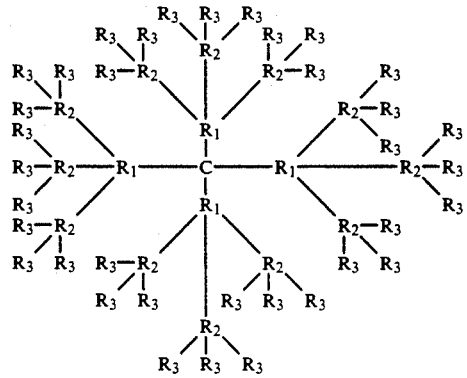

wherein $R_1$ is an alkyl having C3 to C20, $R_2$ is an alkyl having C3 to C20, $R_3$ is selected from the group consisting of —$CONH_2$, —COCl, CHO, —CN, —$CO_2R_4$, —$COR_4$, and $R_4$ is selected from the group consisting of H, alkyl, alkaryl, aryl, ammonium, sulfonium phosphonium and metal salt.

30. A unimolecular micelle having the formula

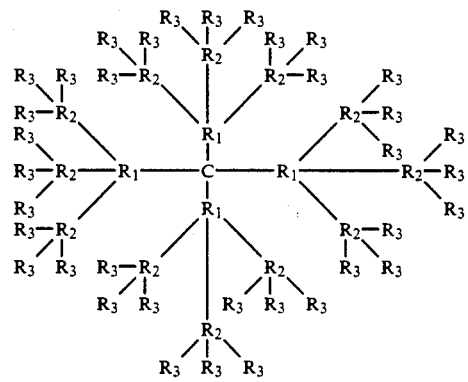

wherein $R_1$ is a perfluoroalkyl having C3–C20, $R_2$ is a perfluoroalkyl having $C_3$ to $C_2$., $R_3$ is selected from the group consisting of F, $CF_3$, $CONH_2$, COCl, CHO, CN, $CO_2R_4$, and $R_4$ is selected from the group consisting of F, $CF_3$ perfluoroalkyl, perfluoroalkaryl, perfluoroaryl ammonium, sulfonium, phosphonium and metal salt.

* * * * *